United States Patent
Olson et al.

(10) Patent No.: US 10,214,488 B2
(45) Date of Patent: Feb. 26, 2019

(54) METHODS OF MANUFACTURING CERTAIN SUBSTITUTED SULFILIMINES

(71) Applicant: Dow AgroSciences LLC, Indianapolis, IN (US)

(72) Inventors: Kurt D. Olson, Freeland, MI (US); Aaron A. Shinkle, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/624,815

(22) Filed: Jun. 16, 2017

(65) Prior Publication Data

US 2017/0362177 A1 Dec. 21, 2017

Related U.S. Application Data

(60) Provisional application No. 62/352,699, filed on Jun. 21, 2016.

(51) Int. Cl.
*C07D 213/34* (2006.01)
*B01J 19/24* (2006.01)

(52) U.S. Cl.
CPC ........ *C07D 213/34* (2013.01); *B01J 19/2435* (2013.01); *B01J 2219/24* (2013.01)

(58) Field of Classification Search
None
See application file for complete search history.

(56) References Cited

U.S. PATENT DOCUMENTS

2014/0163236 A1* 6/2014 Gonzalez ............. C07D 213/34
546/330

OTHER PUBLICATIONS

Synthetic Workstations, Reduce Chemical Times, Easy Max Advanced, pp. 1-2, May (Year: 2014).*

* cited by examiner

*Primary Examiner* — Zinna Northington Davis

(57) ABSTRACT

Provided are methods and/or systems to convert sulfide intermediates to sulfilimines using a series of continuous loop reactors instead of a batch reactor. The advantages of the methods and systems provided include improved total yield, improved heat management, improved phase mixing, and/or improved volume management.

9 Claims, 1 Drawing Sheet

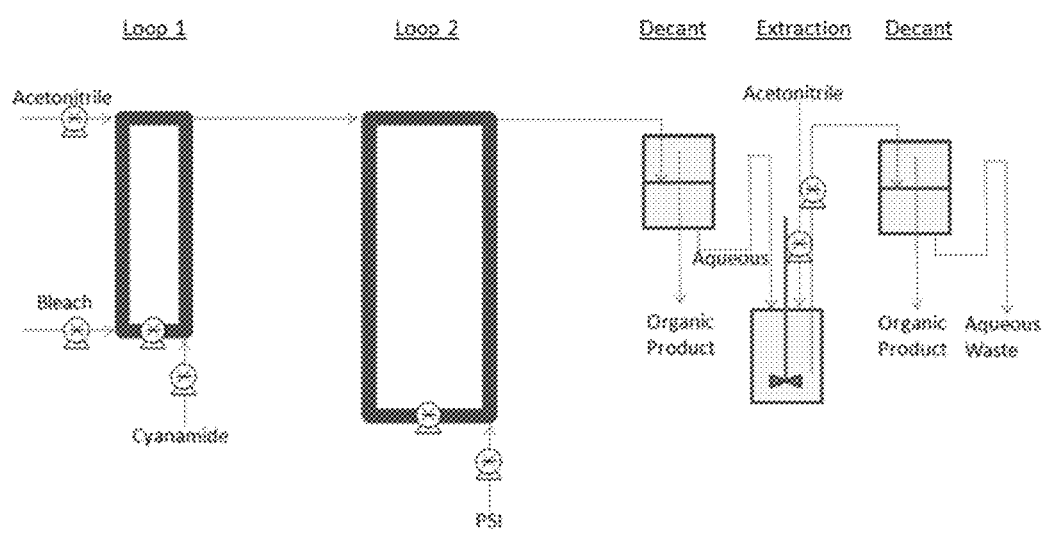

METHODS OF MANUFACTURING CERTAIN SUBSTITUTED SULFILIMINES

CROSS REFERENCE TO RELATED APPLICATIONS

This application claims the benefit of U.S. Provisional Patent Application Ser. No. 62/352,699, filed Jun. 21, 2016

BACKGROUND OF THE INVENTION

The present invention concerns an improved process for manufacturing certain cyano-substituted sulfilimines.

Cyano-substituted sulfilimines are useful intermediates for the preparation of certain new insecticidal sulfoximines; see, for example, U.S. Pat. Nos. 7,678,920 B2 and 7,687,634 B2. U.S. Pat. No. 7,868,027 B2 describes the manufacture of substituted sulfilimines by the reaction of the corresponding sulfide with cyanamide and hypochlorite solution in a suitable organic solvent. While the hypochlorite process of U.S. Pat. No. 7,868,027 B2 is preferable to the iodobenzene diacetate process described in U.S. Pat. Nos. 7,678,920 B2 and 7,687,634 B2, it is plagued by significant levels of byproducts formed by competing reactions of the sulfide starting materials and the sulfilimine products.

Therefore, there is the need for inventions that are useful to produce the substituted sulfilimines efficiently and in higher yields.

SUMMARY OF THE INVENTION

Provided are methods and/or systems to convert sulfide intermediates to sulfilimines using a series of continuous loop reactors instead of a batch reactor. The advantages of the methods and systems provided include improved total yield and increased reaction rate due to improved heat management and improved phase mixing.

In one aspect, provided is a method of preparing a sulfilimine of Formula (I),

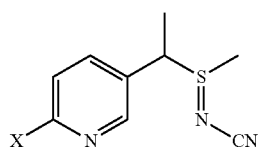

Formula (I)

wherein X represents halogen, $C_1$-$C_4$ alkyl or $C_1$-$C_4$ haloalkyl. The method comprises:
(a) mixing a solution of cyanamide, a solution of hypochlorite, and a solvent in a first continuous loop reactor;
(b) transferring the mixture of Step (a) into a second continuous loop reactor;
(c) adding a sulfide of Formula (II) into the second continuous loop reactor which reacts with the mixture of Step (a) to form the sulfilimine,

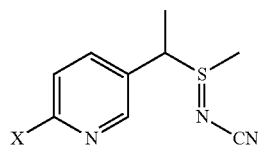

Formula (II)

wherein X is as previously defined; and
(d) decanting the aqueous phase giving an organic phase containing a sulfilimine of Formula (I).

In one embodiment, X represents $CF_3$. In another embodiment, the solvent comprises acetonitrile. In another embodiment, Step (a) is performed at a temperature between −9° C. and +3° C., most preferably −5° C. In another embodiment, Step (c) is performed at a temperature between −15° C. and 0° C., most preferably −5° C. In another embodiment, the cyanamide/hypochlorite mole ratio is between 1.15 and 1.4. In another embodiment, the hypochlorite/sulfide mole ratio is between 1.2 and 1.6. In another embodiment, the solvent/sulfide mass ratio is between 2.5 and 3. In another embodiment, the cyanamide/hypochlorite mole ratio is between 1.2 and 1.3, the hypochlorite/sulfide mole ratio is between 1.2 and 1.5, and/or the solvent/sulfide mass ratio is between 2.5 and 3.

In another aspect, provided is a method of preparing a sulfilimine of Formula (I),

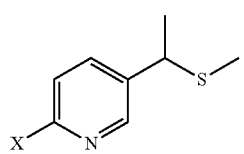

Formula (I)

wherein X represents halogen, $C_1$-$C_4$ alkyl or $C_1$-$C_4$ haloalkyl. The method comprises:
(a) mixing a solution of cyanamide, a solution of hypochlorite, and a solvent in a first continuous loop reactor;
(b) transferring the mixture of Step (a) into a second continuous loop reactor;
(c) adding a sulfide of Formula (II) into the second continuous loop reactor which reacts with the mixture of Step (a) to form the sulfilimine, wherein X is as previously defined;
(d) decanting the aqueous phase giving an organic phase containing a sulfilimine of Formula (1), and
(e) back-extracting the aqueous phase decanted in step (c) with additional solvent to recover additional sulfilimine of Formula (1) to combine with the organic phase of step (d).

In one embodiment, step (e) is performed between −3° C. and +3° C. In another embodiment, step (e) is performed continuously with a solvent/aqueous phase feed rate mass ratio between 0.15 and 0.30, most preferably 0.22. In another embodiment, X represents $CF_3$. In another embodiment, the solvent comprises acetonitrile. In another embodiment, Step (a) is performed at a temperature between −9° C. and +3° C., most preferably −5° C. In another embodiment, Step (c) is performed at a temperature between −15° C. and +3° C., most preferably −5° C. In another embodiment, the cyanamide/hypochlorite mole ratio is between 1.15 and 1.4.

In another embodiment, the hypochlorite/sulfide mole ratio is between 1.2 and 1.6. In another embodiment, the nitrile solvent/sulfide mass ratio is between 2.5 and 3. In another embodiment, the cyanamide/hypochlorite mole ratio is between 1.15 and 1.4, the hypochlorite/sulfide ratio is between 1.2 and 1.6, and/or the nitrile solvent/sulfide mass ratio is between 2.5 and 3.

In another aspect, provided is a method of reducing solid formation and/or gas release after a conversion reaction from a sulfide of Formula (II),

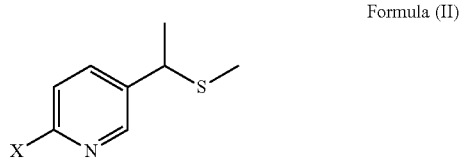

Formula (II)

wherein X represents halogen, $C_1$-$C_4$ alkyl or $C_1$-$C_4$ haloalkyl, into a sulfilimine of Formula (I),

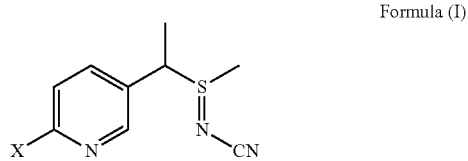

Formula (I)

wherein X is as previously defined. The method comprises quenching the organic solution produced by a conversion reaction, aqueous decant and, optionally back-extraction of the decanted aqueous phase, by raising the temperature of the organic solution to between 50° C. and 95° C. and/or feeding a solution of sulfur dioxide, or sodium bisulfite, or aqueous acid to adjust the pH to a range of between 1 and 6, or aqueous base to adjust the pH to a range of between 8 and 12.

In one embodiment, the quenching step comprises raising the temperature between 50° C. and 95° C. and feeding a solution of sulfur dioxide. In another embodiment, the back-extraction is performed between −3° C. and +3° C. In another embodiment, the back-extraction is performed continuously with a solvent/aqueous phase feed rate mass ratio between 0.15 and 0.30, most preferably 0.22. In another embodiment, X represents $CF_3$. In another embodiment, the solvent comprises acetonitrile. In another embodiment, mixing a solution of cyanamide, a solution of hypochlorite, and a solvent in a first continuous loop reactor is performed at a temperature between −9° C. and +3° C., most preferably −5° C. In another embodiment, adding a sulfide of Formula (II) into the second continuous loop reactor which reacts with the mixture of Step (a) to form the sulfilimine is performed at a temperature between −15° C. and +3° C., most preferably −5° C. In another embodiment, the cyanamide/hypochlorite mole ratio is between 1.15 and 1.4. In another embodiment, the hypochlorite/sulfide mole ratio is between 1.2 and 1.6. In another embodiment, the nitrile solvent/sulfide mass ratio is between 2.5 and 3. In another embodiment, the cyanamide/hypochlorite mole ratio is between 1.15 and 1.4, the hypochlorite/sulfide mole ratio is between 1.2 and 1.6, and/or the nitrile solvent/sulfide mass ratio is between 2.5 and 3.

BRIEF DESCRIPTION OF THE DRAWING

FIG. 1 shows a representative embodiment of the systems provided with two loop reactors.

DETAILED DESCRIPTION OF THE INVENTION

Provided are methods and systems where the conversion of sulfide intermediate to sulfilimine can be performed in a series of continuous loop reactors instead of a batch reactor affording improved heat management, improved phase mixing, and smaller volumes. Several key process variables affecting performance (yield and operability) are also provided herein. For example, the cold temperatures and the separation of bleach oxidation reaction step from the sulfilimine forming step generates sulfilimine solutions that, when used for the manufacture of insecticidal sulfoximine, enables improvements to the crystallization of insecticidal sulfoximine by reducing sulfoxide impurities in insecticidal sulfoximine resulting in 8% higher yields in the conversion of pyridine sulfide to insecticidal sulfoximine.

Existing methods to make sulfilimine from pyridine sulfide intermediate involve mixing cyanamide, acetonitrile, and pyridine sulfide intermediate into one pot followed by continuous addition of bleach, controlling the rate of heat generation by the rate of bleach addition. The reaction is extremely exothermic so heat removal is rate limiting. The reaction temperature must be as cold as possible because byproduct formation increases at higher temperature. A significant side reaction is the reaction of bleach with the pyridine sulfide intermediate present in the pot to generate a sulfoxide. The resulting mixture contains approximately 8-10% sulfoxide relative to the remaining sulfilimine, and less than 1% of additional impurities. The improvement provided herein results, in part, by pre-mixing bleach, acetonitrile, and cyanamide in a first continuous loop reactor. The bleach is nearly entirely consumed in the first loop reactor. The effluent from that the first loop reactor becomes a reactant in the second (and subsequent) loop reactor along with pyridine sulfide. Significantly, no bleach is fed to second reactor.

Other previously disclosed methods to prepare sulfilimine were performed in a batch reactor by addition of bleach and cyanamide first to produce a reaction intermediate, cyanamide chloride, then adding PSI after the reaction is done or while the reaction is occurring. Significantly, cyanamide chloride has very limited thermal stability at temperatures that can be achieved, and it is largely decomposed before the completion of the addition of pyridine sulfide intermediate. The methods and systems provided by the current invention have advantages over the prior art in that the heat transfer capabilities of the loop reactor design enable extremely short residence times and low temperatures, thereby nearly eliminating decomposition of the cyanamide chloride intermediate reducing impurity levels caused by higher temperature.

The use of bleach at optimal levels introduces water to the reaction system forming a two-phase system. The presence of an aqueous phase in processes to prepare sulfilimine can reduce the yield by extracting some of the sulfilimine from the organic, product-containing phase into the waste aqueous phase. The present invention provides a method whereby the loss of sulfilimine to the aqueous phase can be reduced. The aqueous layer from the initial decant is brought into contact with additional organic solvent which extracts the majority of the sulfilimine from the aqueous layer. The second solvent layer can be combined with the first decant solvent layer, providing a means of recovering additional sulfilimine.

The use of cyanamide in excess to bleach and to pyridine sulfide intermediate results in excess oxidizing equivalent that can further react to form solids and gaseous products which are detrimental to operation of processes to prepare sulfilimine. The present invention provides a method whereby the formation of these solids and gaseous products can be reduced. Analytical work identified the solids as complexes containing multiple cyanamide molecules, and the gas as mostly carbon dioxide. Because the presence of the solid formation and gas release would negatively affect the efficiency of the methods and/or systems provided, different ways of quenching the reaction prevent such solid formation/gas release. Several methods are identified as appropriate quench agents. For example heat treatment at 75° C. for approximately five hours or at 95° C., for two hours. Chemical additives such as sulfur dioxide, sodium metabisulfite, hydrochloric acid, and sodium hydroxide were found effective. The most effective was sulfur dioxide.

Throughout this document, all temperatures are given in degrees Celsius, and all percentages are weight percentages unless otherwise stated.

The term "alkyl", as well as derivative terms such as "haloalkyl", as used herein, include within their scope straight chain, branched chain and cyclic moieties. Thus, typical alkyl groups are methyl, ethyl, 1-methyl-ethyl, propyl, 1,1-dimethylethyl, and cyclo-propyl-.

The term "haloalkyl" includes alkyl groups substituted with from one to the maximum possible number of halogen atoms, all combinations of halogens included.

The term "halogen" or "halo" includes fluorine, chlorine, bromine and iodine, with fluorine being preferred.

The sulfide starting materials or processes for their preparation have been disclosed in for example U.S. Pat. Nos. 7,678,920 B2 and 7,687,634 B2, and U.S. patent application publication US2014/0163236, where the most preferred sulfide is 3-[1-(methylthio)ethyl]-6-(trifluoromethyl)pyridine. The contents of which are thereby incorporated by reference in their entireties.

Cyanamide can be used as an aqueous solution, where the use of a 50 weight percent solution of cyanamide in water is often preferred.

Hypochlorite can be used as an aqueous solution of a metallic salt of hypochlorous acid. The metallic salt can be a Group I alkali metal salt or a Group II alkaline earth metal salt. The preferred hypochlorite salts are sodium hypochlorite or calcium hypochlorite.

The conversion reaction can be conducted in the presence of a solvent, where acetonitrile is often preferred.

The pH of the conversion reaction in the first loop reactor can be controlled from about 7 to 12, with about 8.5 to 9.5 being most preferred.

The pH of the conversion reaction in the second loop reactor can be controlled from about 7 to 12, with about 8 to about 9.5 being most preferred.

The mole ratio of cyanamide/hypochlorite fed to the first loop reactor is between 1.0 and 2.0, preferably between 1.2 and 1.3

The mole ratio hypochlorite fed to the first loop reactor and sulfide fed to the second loop reactor is between 1.0 and 2.5, preferably between 1.2 and 1.5

The mass ratio solvent fed to the first loop reactor and sulfide fed to the second loop reactor is between 1.5 and 5, preferably between 2.5 and 3

The organic solution of the sulfilimine can be used directly in a subsequent oxidation to an insecticidal sulfoximine or the sulfilimine can be isolated and purified by conventional techniques.

In one aspect, provided is a method of preparing a sulfilimine of Formula (I),

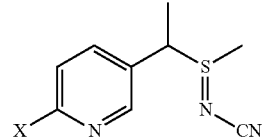

Formula (I)

wherein X represents halogen, $C_1$-$C_4$ alkyl or $C_1$-$C_4$ haloalkyl. The method comprises:

(e) mixing a solution cyanamide, a solution of hypochlorite, and a nitrile solvent in a first continuous loop reactor;

(f) transferring the mixture of Step (a) into a second continuous loop reactor;

(g) reacting the mixture of Step (a) with a sulfide of Formula (II) in the second continuous loop reactor to form the sulfilimine,

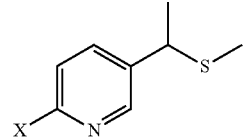

Formula (II)

wherein X is as previously defined; and (h) quenching the reaction of Step (c) with a temperature between 50° C. and 95° C. and/or feeding a solution of sulfur dioxide.

In one embodiment, the quenching step comprises feeding a solution of sulfur dioxide. In another embodiment, the quenching step comprises raising the temperature between 50° C. and 95° C. and feeding a solution of sulfur dioxide. In another embodiment, X represents $CF_3$. In another embodiment, the nitrile solvent comprises acetonitrile. In another embodiment, Step (a) is performed at a temperature between −9° C. and +3° C.; or about −5° C. In another embodiment, Step (c) is performed at a temperature between −3° C. and −5° C.; between −15° C. and 0° C.; or about −5° C. In another embodiment, the cyanamide/hypochlorite mole ratio is between 1.15 and 1.4; between 1.2 and 1.3; or about 1.22. In another embodiment, the hypochlorite/sulfide mole ratio is between 1.2 and 1.6; between 1.2 and 1.5; or about 1.4. In another embodiment, the nitrile solvent/sulfide mole ratio is between 2.5 and 3; or about 2.75. In another embodiment, the cyanamide/hypochlorite mole ratio is between 1.2 and 1.3, the hypochlorite/sulfide mole ratio is between 1.2 and 1.5, and/or the solvent/sulfide mass ratio is between 2.5 and 3. In another embodiment, the cyanamide/hypochlorite mole ratio is about 1.22, the hypochlorite/sulfide mole ratio is about 1.4, and/or the nitrile solvent/sulfide mole ratio is about 2.75.

In another aspect, provided is a system of preparing a sulfilimine of Formula (I),

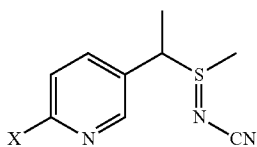

Formula (I)

wherein X represents halogen, $C_1$-$C_4$ alkyl or $C_1$-$C_4$ haloalkyl. The system comprises:
(a) a first continuous loop reactor configured to receive a solution cyanamide, a solution of hypochlorite, and a nitrile solvent;
(b) a second continuous loop reactor configured to receive a mixture from the first continuous loop reactor and a sulfide of Formula (II),

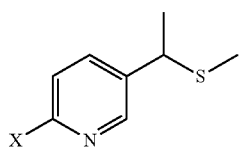

Formula (II)

wherein X is as previously defined;
(c) a pressure means for transfering the mixture from the first continuous loop reactor into the second continuous loop reactor; and
(d) a temperature means for lowering the temperature of the second continuous loop reactor between −3° C. and −5° C. and/or raising the temperature of the second continuous loop reactor between 50° C. and 95° C.

In another aspect, provided is a system of preparing a sulfilimine of Formula (I),

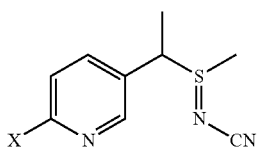

Formula (I)

wherein X represents halogen, $C_1$-$C_4$ alkyl or $C_1$-$C_4$ haloalkyl. The system comprises:
(a) a first continuous loop reactor configured to receive a solution cyanamide, a solution of hypochlorite, and a nitrile solvent;
(b) a second continuous loop reactor configured to receive a mixture from the first continuous loop reactor and a sulfide of Formula (II),

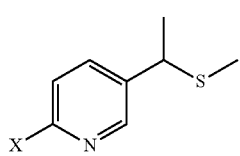

Formula (II)

wherein X is as previously defined;
(c) a pressure panel configured to transfer the mixture from the first continuous loop reactor into the second continuous loop reactor; and
(d) a temperature panel configured to lower the temperature of the second continuous loop reactor between −3° C. and −5° C. and/or raise the temperature of the second continuous loop reactor between 50° C. and 95° C.

In one embodiment, the system provided further comprises a feed for adding a solution of sulfur dioxide into the second continuous loop reactor. In another embodiment, X represents $CF_3$. In another embodiment, the nitrile solvent comprises acetonitrile. In another embodiment, the cyanamide/hypochlorite mole ratio is between 1.15 and 1.4; between 1.2 and 1.3; or about 1.22. In another embodiment, the hypochlorite/sulfide mole ratio is between 1.2 and 1.6; between 1.2 and 1.5; or about 1.4. In another embodiment, the nitrile solvent/sulfide mole ratio is between 2.5 and 3; or about 2.75. In another embodiment, the cyanamide/hypochlorite mole ratio is between 1.2 and 1.3, the hypochlorite/sulfide mole ratio is between 1.2 and 1.5, and/or the solvent/sulfide mass ratio is between 2.5 and 3. In another embodiment, the cyanamide/hypochlorite mole ratio is about 1.22, the hypochlorite/sulfide mole ratio is about 1.4, and/or the nitrile solvent/sulfide mole ratio is about 2.75.

In another aspect, provided is a method of preventing solid formation and/or gas release after a conversion reaction from a sulfide of Formula (II),

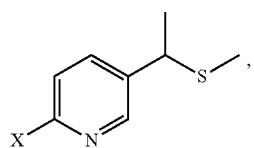

Formula (II)

wherein X represents halogen, $C_1$-$C_4$ alkyl or $C_1$-$C_4$ haloalkyl,
into a sulfilimine of Formula (I),

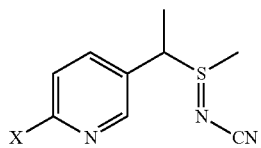

Formula (I)

wherein X is as previously defined. The method comprises quenching the conversion reaction by raising the temperature between 50° C. and 95° C. and/or feeding a solution of sulfur dioxide.

In one embodiment, the quenching step comprises raising the temperature between 50° C. and 95° C. and feeding a solution of sulfur dioxide. In another embodiment, X represents $CF_3$. In another embodiment, the conversion reaction uses a nitrile solvent. In a further embodiment, the nitrile solvent comprises acetonitrile. In another embodiment, the conversion reaction is performed at a temperature between −3° C. and −5° C. In another embodiment, the conversion reaction uses cyanamide and hypochlorite, and the cyanamide/hypochlorite mole ratio is between 1.15 and 1.4; between 1.2 and 1.3; or about 1.22. In another embodiment, the conversion reaction uses hypochlorite and sulfide, and the hypochlorite/sulfide mole ratio is between 1.2 and 1.6; between 1.2 and 1.5; or about 1.4. In another embodiment, the conversion reaction uses a nitrile solvent and sulfide, and the nitrile solvent/sulfide mole ratio is between 2.5 and 3; or about 2.75. In another embodiment, the cyanamide/hypochlorite mole ratio is between 1.2 and 1.3, the hypochlorite/sulfide mole ratio is between 1.2 and 1.5, and/or the solvent/sulfide mass ratio is between 2.5 and 3. In another embodiment, the cyanamide/hypochlorite mole ratio is about 1.22, the hypochlorite/sulfide mole ratio is about 1.4, and/or the nitrile solvent/sulfide mole ratio is about 2.75.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

EXAMPLES

Example 1

Two loop reactors are used in series as shown in FIG. 1. The feed materials used include 12% bleach in water, 99.99% acetonitrile, process recycled acetonitrile, 50% cyanamide in water, and 96+% Pyridine sulfide intermediate (PSI).

Acetonitrile, bleach and cyanamide are fed with Cole Parmer peristaltic pumps to the first loop reactor. Temperature, pressure, and pH are monitored during the experiment. The following ranges of variables are tested for the first loop reactor:
Cyanamide/Bleach mole ratios between 1.15 and 1.8
Acetonitrile/PSI mass ratios between 2.5 and 4.5
Residence time between 0.75 minutes and 4.5 minutes
Temperature between −9° C. and +5° C.
pH between 7.5 and 10
Acetonitrile acidity between 0 and 300 mm H$^+$/kg solvent
Reynolds number between 500 and 4500

The second loop reactor adds PSI to the reaction mixture through an ISCO syringe pump. The second loop reactor also has a 25 psi check valve to hold back pressure on the pumps. The following ranges of variables are tested for the second loop reactor:
Bleach/PSI mole ratios between 1.2 and 1.8
Residence time between 2.5 minutes and 15 minutes
Temperature between −13° C. and +3° C.
pH between 8 and 9
Reynolds number between 500 and 4500

A continuous decanter is added after the second loop to separate the organic and aqueous phases inline. The aqueous phase then goes to a mixed vessel with an addition port for acetonitrile to mix the solution in which product is extracted out of the water phase. The two phase mixture then goes to a second decanter which separates the layers. The decanters are ~200 mL vessels that are jacketed and cooled to 0° C. A standpipe down the center of the vessel controls the overall liquid height where organic phase comes off overhead. A gravity leg controls the position of the interface relative to the surface and is intended to lie close to the center of the vessel. The final product is the mixture of both organic phases which can be directly passed forward in the process. The following ranges of variables are tested for the separations vessels:
Solvent/feed mass ratio between 0 and 0.21
Residence time between 5 minutes and 30 minutes
Temperature between −5° C. and +10° C.

Previously disclosed methods for preparing sulfilimine recommend a running temperature between −5° C. and −15° C. as a slurry reaction in a batch reactor. However, such low temperatures may result in freezing of the aqueous phase in loop reactors used here. Accordingly, subsequent experiments using the loop reactors are performed between −3° C. and −5° C. with significant heat exchanger area to keep the temperature difference between the wall and process fluid to a minimum.

Example 2

Two loop reactors are used in series as shown schematically in FIG. 1. The feed materials used include 12% bleach in water, 99.99% acetonitrile, process recycled acetonitrile (contains approximately 15% water, 0.5% chloroform, 0.5% toluene, and 100 mmol acid/kg solution), 50% cyanamide in water, and 96+% pyridine sulfide intermediate (PSI).

Acetonitrile, bleach and cyanamide are fed with Cole Parmer peristaltic pumps to the first loop reactor. Temperature, pressure, and pH are monitored during the experiment. The values of variables for the first loop reactor are:
Cyanamide/Bleach mole ratio 1.22
Acetonitrile/PSI mass ratio 2.75
Residence time 2 minutes
Temperature −3° C.

The second loop reactor adds PSI to the reaction mixture through an ISCO syringe pump. The second loop reactor also has a 25 psi check valve to hold back pressure on the pumps. The variables for the second loop reactor are:
Bleach/PSI mole ratio 1.22
Residence time 5 minutes
Temperature −5° C.

A continuous decanter after the second loop to separates the organic and aqueous phases. The aqueous phase is gravity fed to a mixed vessel with an addition port for acetonitrile. The two phase mixture then is pumped by peristaltic pump to a second decanter which separates the aqueous and organic layers. The decanters are ~200 mL vessels that are jacketed and cooled to 0° C. A standpipe down the center of the vessel controls the overall liquid height where organic phase comes off overhead. A gravity leg controls the position of the interface relative to the surface and is intended to lie close to the center of the vessel. The final product is the combination of organic phases from the first and second decanters and can be directly passed forward in the process. The following ranges of variables are tested for the separations vessels:
Solvent/feed mass ratio 0.21
Residence time 10 minutes
Temperature 0° C.

When the product solution prepared at these conditions is used as starting material in the next process step (oxidation of the sulfilimine to generate a sulfoximine), optimal oxidation conditions give a sulfoximine yield of 85%. The experimental conditions described above use the same stoichiometry as the commercially practiced semi batch operation which, after oxidation under optimal condition, generates a sulfoximine yield of only 74.4%.

Example 3

In this example, the reactant stoichiometries are varied slightly from Examples 1 and 2. Unless specified, the conditions are the exact same as Example 2. The results are shown in Table 1.

TABLE 1

Overall yield obtained from runs varying the stoichiometry and crystallization water loading

| Experiment # | Cyanamide/Bleach ratio | Bleach/PSI ratio | Overall Sulfoximine Yield After Oxidation |
|---|---|---|---|
| 3-1 | 1.22 | 1.5 | 85.2% |
| 3-2 | 1.22 | 1.25 | 85.6% |
| 3-3 | 1.3 | 1.5 | 82.6% |
| 3-4 | 1.22 | 1.4 | 83.4% |

Example 4

This example compares data with and without back extraction. The loop reactors are run with cyanamide/bleach mole ratio of 1.45, Acetonitrile/PSI mass ratio of 2.75 in loop 1 (unless specified), and bleach/PSI ratio of 1.2. The first reactor is run at −3° C. with flowrates such that the residence time is two minutes. The second reactor is run at −5° C. with flowrates such that the residence time is five minutes. The separation equipment has a solvent/feed mass ratio of 0.21 (unless specified) with a ten minute residence time and temperature near 0° C. Table 2 shows the results of this experiment when varying the solvent/feed ratio.

TABLE 2

Yield loss to aqueous phase and product recovery versus amount of acetonitrile in the back extraction

| Experiment # | Solvent/Feed [g/g] | Yield in aqueous % | Recovery wt % |
|---|---|---|---|
| 4-1 | 0.41 | 0.11 | 96.7 |
| 4-2 | 0.10 | 0.48 | 84.1 |
| 4-3 | 0.21 | 0.29 | 91.0 |
| 4-4 | 0.41 | 0.13 | 95.9 |
| 4-5 | 0.00 | 2.38 | 0.0 |
| 4-6 | 0.00 | 2.27 | 0.0 |
| 4-7 | 0.00 | 2.6 | 0.0 |
| 4-8 | 0.31 | 0.19 | 93.6 |

Table 3 shows the results where the bleach/PSI mole ratio is changed to illustrate the importance of the back extract with the amount of water added to the system.

TABLE 3

Yield loss to aqueous phase versus amount of bleach added to the loop reactor

| Experiment # | Bleach/PSI mole ratio | Yield in aqueous % |
|---|---|---|
| 4-9 | 1.2 | 0.19 |
| 4-10 | 1.3 | 0.32 |
| 4-11 | 1.4 | 0.24 |
| 4-12 | 1.6 | 0.65 |

Example 5

In previous experiments, significant solid formation appears when a large amount of bleach excess is used. In addition, if the aqueous phase is not quenched after the completion of the process, both solid (complexes containing multiple cyanamide molecules) formation and gas (carbon dioxide) release appear in the aqueous phase. An experiment is performed to observe the effect of additives on the aqueous samples. The loop reactors are run under the conditions described according to Example 2 and with an increased bleach/PSI mole ratio of 1.4. The resulting aqueous phase is immediately removed from the tail of the reactor and placed into jars subjecting the material to different conditions.

TABLE 4

Amount of solids precipitated from an aqueous solution two weeks after treatment

| | | % solids | |
|---|---|---|---|
| Experiment # | Treatment | 1.22 bleach/PSI | 1.4 bleach/PSI |
| 4-1 | None | 0.13 | 0.62 |
| 4-2 | Sodium Metabisulfite | 0.13 | 0.22 |
| 4-3 | Sulfur dioxide | 0.03 | 0.03 |
| 4-4 | Heat to 75° C. | 0.10 | 0.57 |
| 4-5 | Strip acetonitrile | 0.12 | 0.00 |
| 4-6 | Add acid then strip acetonitrile | 0.00 | 0.73 |
| 4-7 | Add base then strip acetonitrile | 0.10 | 0.49 |

Table 4 shows how the amount of solids (as measured two weeks after the treatment) change with the different conditions they are subjected to, where the mass of solids is expressed as a percent versus the total amount of aqueous added. 4-1 is a control sample with no treatment performed. 4-2 and 4-3 involve addition of either solid sodium metabisulfite or 6% sulfur dioxide in water solution until starch iodide paper indicates no further oxidation strength. For 4-4, the solution is heated to 75° C. at atmospheric pressure and the temperature is controlled at that point until starch iodide paper indicates no further oxidation strength. 4-5 involves heating the aqueous phase until it boils and remove the volatiles. Heating is stopped when starch iodide paper indicates no further oxidation strength. 4-6 and 4-7 involve addition of hydrochloric acid until the solution is pH 3 or sodium hydroxide until the pH is 10 then perform the same action as the fifth entry where volatiles are stripped from the solution.

We claim:

1. A method of preparing a sulfilimine of Formula (I),

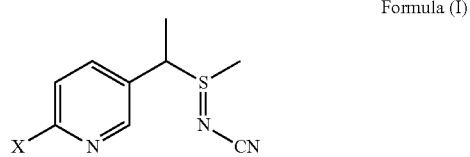

Formula (I)

wherein X represents halogen, $C_1$-$C_4$ alkyl or $C_1$-$C_4$ haloalkyl; comprising, (a) mixing a solution cyanamide, a solution of hypochlorite, and a solvent in a first continuous loop reactor;

(b) transferring the mixture of Step (a) into a second continuous loop reactor;

(c) adding a sulfide of Formula (II) into the second continuous loop reactor which reacts with the mixture of Step (a) to form the sulfilimine,

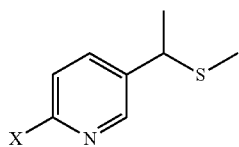

Formula (II)

wherein X is as previously defined; and (d) decanting the aqueous phase giving an organic phase containing a sulfilimine of Formula (I).

2. The method of claim 1, wherein X represents $CF_3$.

3. The method of claim 1, wherein the solvent comprises acetonitrile.

4. The method of claim 1, wherein Step (a) is performed at a temperature between −9° C. and 5° C.

5. The method of claim 1, wherein Step (a) is performed at a temperature between −5° C. and −3° C.

6. The method of claim 1, wherein Step (c) is performed at a temperature between −13° C. and 3° C.

7. The method of claim 1, wherein Step (c) is performed at a temperature between −5° C. and −3° C.

8. The method of claim 1, wherein the cyanamide/hypochlorite mole ratio is between 1.0 and 2.0, the hypochlorite/sulfide mole ratio is between 1.0 and 2.5, and/or the acetonitrile solvent/sulfide mass ratio is about between 1.5 and 5.

9. The method of claim 1, wherein the cyanamide/hypochlorite mole ratio is between 1.15 and 1.4, the hypochlorite/sulfide mole ratio is between 1.2 and 1.5, and/or the acetonitrile solvent/sulfide mass ratio is about between 2.5 and 3.

\* \* \* \* \*